United States Patent [19]

Brouwer et al.

[11] Patent Number: 4,656,193
[45] Date of Patent: Apr. 7, 1987

[54] BENZOYLUREA COMPOUNDS, AND INSECTICIDAL AND ACARICIDAL COMPOSITIONS COMPRISING SAME

[75] Inventors: Marius S. Brouwer; Arnoldus C. Grosscurt; Roelof van Hes, all of Weesp, Netherlands

[73] Assignee: Duphar International Research B.V., Weesp, Netherlands

[21] Appl. No.: 778,433

[22] Filed: Sep. 20, 1985

Related U.S. Application Data

[63] Continuation-in-part of Ser. No. 572,142, Jan. 19, 1984.

[30] Foreign Application Priority Data

Jan. 24, 1983 [NL] Netherlands ............... 8300239

[51] Int. Cl.⁴ ............... C07C 127/22; A01N 47/34
[52] U.S. Cl. ............................. 514/594; 564/44
[58] Field of Search ........................ 564/44; 514/594

[56] References Cited

U.S. PATENT DOCUMENTS

| | | | |
|---|---|---|---|
| 3,748,356 | 7/1973 | Wellinga et al. | 564/44 |
| 4,068,002 | 1/1978 | Sirrenberg et al. | 564/44 |
| 4,350,706 | 9/1982 | Brouwer et al. | 564/44 |
| 4,426,385 | 1/1984 | Cain | 564/44 |

Primary Examiner—Charles F. Warren
Assistant Examiner—C. S. Greason
Attorney, Agent, or Firm—Stevens, Davis, Miller & Mosher

[57] ABSTRACT

The invention relates to new benzoylurea compounds of the general formula

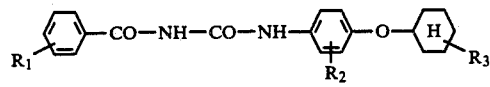

wherein
$R_1$ is a hydrogen atom or represents 1 or 2 substituents which are selected from the group consisting of halogen and alkyl and haloalkyl having 1-4 carbon atoms,
$R_2$ is a hydrogen atom or represents 1 or 2 substituents which are selected from the group consisting of chlorine, methyl and trifluoromethyl, and
$R_3$ is a hydrogen atom or represents 1-3 alkyl and/or alkenyl groups each having 1-6 and/or 2-6 carbon atoms respectively,
or wherein $R_3$ together with the cyclohexyl ring to which it is attached forms a bi- or polycyclic hydrocarbyl group having 8-14 carbon atoms and, if desired, substituted with 1-3 alkyl groups each having 1-4 carbon atoms.

The compounds have an insecticidal and acaricidal activity. After having been processed to compositions, the compounds may be used for the control of insects and/or mites in a dosage from 1 to 5000 g of active substance per hectare.

9 Claims, No Drawings

BENZOYLUREA COMPOUNDS, AND INSECTICIDAL AND ACARICIDAL COMPOSITIONS COMPRISING SAME

REFERENCE TO RELATED APPLICATIONS

This application is a continuation in part of copending application Ser. No. 572,142, filed Jan. 19, 1984.

PRESENT INVENTION

The present invention relates to new benzoylurea compounds and to a method of preparing said compounds. The invention also relates to compositions having insecticidal and acaricidal activities and comprising these compounds, and to the use of said compositions for controlling insects and/or mites.

It is already known that certain N-benzoyl-N'-phenylurea compounds have an insecticidal activity. From Netherlands Patent Application 7105350 it appears that in particular the substitution pattern of the benzoyl group has an important influence on said activity. In general, a high insecticidal activity is found in benzoylurea compounds the benzoyl group of which is substituted in the 2- or 2,6-positions, for example, with one or two halogen atoms. Substituents on the other side of the molecule, i.e., in the N'-phenyl ring, are less essential for the insecticidal activity but can nevertheless influence said activity in such manner that the benzoylurea compound is better or worse suitable for practical applications. For example, it appears from an article by Wellinga et al. in J. Agr. Food Chem., Vol 21, No. 3, 1973, pp. 348–354, that electrons-donating substituents on the N'-phenyl ring, for example, a methoxy group, adversely influence the insecticidal activity.

It has surprisingly been found that benzoylurea compounds having a cyclohexyloxy group substituted or not substituted with one or more alkyl, alkenyl or cycloalkyl groups as substituents on the N'-phenyl ring have an interesting insecticidal activity. Moreover, an acaricidal activity is also found in the new benzoylurea compounds according to the invention.

In addition it has been found that the cyclohexyloxyphenylurea compounds of the invention even show an interesting activity when the 2- or 2,6-substitution pattern (see above) in the benzoyl group is not present. This is contrary to the expectation, especially in view of what is disclosed by Wellinga et al. in J. Agr. Food Chem., Vol. 21 No. 3, 1973, pp. 348–354.

Chemically related benzoylurea compounds are described in the Netherlands Patent Application 7905155, e.g. N-(2-chlorobenzoyl)-N'-[4-(1-phenylcyclohexyloxy)phenyl]urea.

As will be clear from the Examples, this known compound is considerably less active than the new compounds of the present invention.

This invention relates to benzoylurea compounds of the general formula

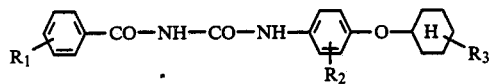

(I)

wherein
R$_1$ is a hydrogen atom or represents 1 or 2 substituents which are selected from the group consisting of halogen and alkyl and haloalkyl having 1–4 carbon atoms.

R$_2$ is a hydrogen atom or represents 1 or 2 substituents which are selected from the group consisting of chlorine, methyl and trifluoromethyl, and R$_3$ is a hydrogen atom or represents 1–3 alkyl and/or alkenyl groups each having 1–6 and/or 2–6 carbon atoms respectively, or wherein R$_3$ together with the cyclohexyl ring to which it is attached forms a bi- or polycyclic hydrocarbyl group having 8–14 carbon atoms and, if desired, substituted with 1–3 alkyl groups each having 1–4 carbon atoms.

These compounds have an interesting insecticidal and acaricidal activity and have a wide activity spectrum as will become apparent from the examples.

An alkyl, alkenyl or cycloalkyl group on the ortho-position of the cyclohexyloxy group generally even increases the insecticidal activity. Therefore, benzoylurea compounds are to be preferred which satisfy the general formula

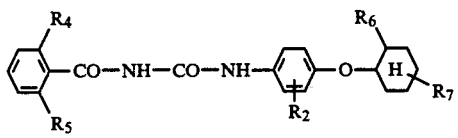

wherein
R$_2$ has the above meaning,
R$_4$ is a halogen atom or a methyl group,
R$_5$ is a hydrogen atom or a halogen atom,
R$_6$ is an alkyl or alkenyl group having 1–4 or 2–4 carbon atoms respectively, and
R$_7$ is a hydrogen atom or an alkyl or alkenyl group having 1–4 or 2–4 carbon atoms respectively, or wherein
R$_6$ and R$_7$ together with the cyclohexyl ring to which they are attached form a 2-bornyl or 2-adamantyl group.

Of the last-mentioned compounds, the menthyloxy compounds, in particular N-(2,6-difluorobenzoyl)-N'-(4-menthyloxyphenyl)urea and N'-(2-chlorobenzoyl)-N'-(4-menthyloxyphenyl)urea have proved excellently suitable, not only due to the high insecticidal activity but also due to the ready availability of the raw materials.

These menthyloxy compounds may occur in two stereoisomers, namely the d- and the l-form, while of course mixtures of these stereoisomers are also possible. If desired, the stereoisomers can be separated from each other by methods known for this purpose, bur for practical considerations the use of a sterically pure cyclohexanol derivative is to be preferred as a starting material for the preparation of one of the stereoisomers in a pure form. Examples of new benzoylurea compounds according to the invention are:

(1) N-(2,6-difluorobenzoyl)-N'-(4-dl-menthyloxyphenyl)urea,
(2) N-(2,6-difluorobenzoyl)-N'-(4-d-menthyloxyphenyl)urea,
(3) N-(2-chlorobenzoyl)-N'-(4-dl-menthyloxyphenyl)urea,
(4) N-(2-chlorobenzoyl)-N'-(4-d-menthyloxyphenyl)urea,
(5) N-(2,6-difluorobenzoyl)-N'-(4-l-menthyloxyphenyl)urea, (6) N-(2-chlorobenzoyl)-N'-(4-l-menthyloxyphenyl)urea,
(7) N-(2-methylbenzoyl)-N'-(4-dl-menthyloxyphenyl)urea,
(8) N-benzoyl-N'-(4-dl-menthyloxyphenyl)urea,
(9) N-benzoyl-N'-(3-chloro-4-dl-menthyloxyphenyl)urea,
(10) N-(2-chlorobenzoyl)-N'-(3-chloro-4-dl-menthyloxyphenyl)urea,
(11) N-(2,6-difluorobenzoyl)-N'-(3-chloro-4-dl-menthyloxyphenyl)urea,
(12) N-benzoyl-N'-(3-methyl-4-dl-menthyloxyphenyl)urea,
(13) N-(2-chlorobenzoyl)-N'-(3-methyl-4-dl-menthyloxyphenyl)urea,
(14) N-(2,6-difluorobenzoyl)-N'-(3-methyl-4-dl-menthyloxyphenyl)urea,
(15) N-(2-chlorobenzoyl)-N'-(4-cyclohexyloxyphenyl)urea,
(16) N-(2-methylbenzoyl)-N'-(4-cyclohexyloxyphenyl)urea,
(17) N-(2,6-difluorobenzoyl)-N'-(4-cyclohexyloxyphenyl)urea,
(18) N-(2-chlorobenzoyl)-N'-[4-(2-methylcyclohexyloxy)phenyl]urea,
(19) N-(2-methylbenzoyl)-N'-[4-(2-methylcyclohexyloxy)phenyl]urea,
(20) N-(2,6-difluorobenzoyl)-N'-[4-(2-methylcyclohexyloxy)phenyl]urea,
(21) N-benzoyl-N'-[4-(2-ethylcyclohexyloxy)phenyl]urea,
(22) N-(2-chlorobenzoyl)-N'-[4-(2-ethylcyclohexyloxy)phenyl]urea,
(23) N-(2,6-difluorobenzoyl)-N'-[4-(2-ethylcyclohexyloxy)phenyl]urea,
(24) N-benzoyl-N'-[4-(2-tert.-butylcyclohexyloxy)phenyl]urea,
(25) N-(2-chlorobenzoyl)-N'-[4-(2-tert.-butylcyclohexyloxy)phenyl]urea,
(26) N-(2,6-difluorobenzoyl)-N'-[4-(2-tert.-butylcyclohexyloxy)phenyl]urea,
(27) N-benzoyl-N'-[4-(2,6-dimethylcyclohexyloxy)phenyl]urea,
(28) N-(2-chlorobenzoyl-N'-[4-(2,6-dimethylcyclohexyloxy)phenyl]urea,
(29) N-(2,6-difluorobenzoyl)-N-[4-(2,6-dimethylcyclohexyloxy)phenyl]urea,
(30) N-(2-chlorobenzoyl)-N'-[3-methyl-4(2-ethylcyclohexyloxy)phenyl]urea,
(31) N-(2,6-difluorobenzoyl)-N'-[3-methyl-4-(2-ethylcyclohexyloxy)phenyl]urea,
(32) N-(2-chlorobenzoyl)-N'-[4-bornyl(-2)oxyphenyl]urea,
(33) N-(2,6-difluorobenzoyl)-N'-[4-bornyl(-2)oxyphenyl]urea,
(34) N-benzoyl-N'-[3-methyl-4-bornyl(-2)oxyphenyl]urea,
(35) N-(2-chlorobenzoyl)-N'-[3-methyl-4-bornyl(-2)oxophenyl]urea,
(36) N-(2,6-difluorobenzoyl)-N'-[3-methyl-4-bornyl(-2)oxophenyl]urea,
(37) N-benzoyl-N'-(3-trifluoromethyl-4-dl-menthyloxyphenyl)urea,
(38) N-(2-chlorobenzoyl)-N'-(3-trifluoromethyl-4-dl-menthyloxyphenyl)urea,
(39) N-(2,6-difluorobenzoyl)-N'-(3-trifluoromethyl-4-dl-menthyloxyphenyl)urea,
(40) N-benzoyl-N'-[4-(2-isopropenyl-5-methylcyclohexyloxy)phenyl]urea,
(41) N-(2-chlorobenzoyl)-N'-[4-(2-isopropenyl-5-methylcyclohexyloxy)phenyl]urea,
(42) N-(2,6-difluorobenzoyl)-N'-[4-(2-isopropenyl-5-methylcyclohexyloxy)phenyl]urea,
(43) N-benzoyl-N'-[4-bornyl(-2)oxyphenyl]urea,
(44) N-benzoyl-N'-[3-chloro-4-bornyl(-2)oxyphenyl]urea,
(45) N-(2-chlorobenzoyl-N'-[3-chloro-4-bornyl(-2)oxyphenyl]urea,
(46) N-(2,6-difluorobenzoyl)-N'-[3-chloro-4-bornyl(-2)oxyphenyl]urea,
(47) N-benzoyl-N'-[4-adamantyl(-2)oxyphenyl]urea,
(48) N-(2-chlorobenzoyl)-N'-[4-adamantyl(-2)oxyphenyl]urea,
(49) N-(2,6-difluorobenzoyl)-N'-[4-adamantyl(-2)oxyphenyl]urea,
(50) N-(4-chlorobenzoyl)-N'-(4-dl-menthyloxyphenyl)urea,
(51) N-(4-trifluoromethylbenzoyl)-N'-(4-dl-menthyloxyphenyl)urea,
(52) N-(3,5-dichlorobenzoyl)-N'-(4-dl-menthyloxyphenyl)urea,
(53) N-(4-fluorobenzoyl)-N'-(4-dl-menthyloxyphenyl)urea,
(54) N-(3,4-dichlorobenzoyl)-N'-(4-dl-menthyloxyphenyl)urea,
(55) N-(4-bromobenzoyl)-N'-(4-dl-menthyloxyphenyl)urea,
(56) N-(3-bromobenzoyl)-N'-(4-dl-menthyloxyphenyl)urea,
(57) N-(2,4-difluorobenzoyl)-N'-(4-dl-menthyloxyphenyl)urea,
(58) N-(2-chlorobenzoyl)-N'-(3,5-dichloro-4-l-menthyloxyphenyl)urea,
(59) N-(2,6-difluorobenzoyl)-N-(3,5-dichloro-4-l-menthyloxyphenyl)urea,
(60) N-(2-chlorobenzoyl)-N'-(3,5-dichloro-4-dl-menthyloxyphenyl)urea,
(61) N-(2,6-difluorobenzoyl)-N'-(3,5-dichloro-4-dl-menthyloxyphenyl)urea,
(62) N-(benzoyl-N'-(4-isomenthyloxyphenyl)urea,
(63) N-(2-chlorobenzoyl)-N'-(4-isomenthyloxyphenyl)urea,
(64) N-(2,6-difluorobenzoyl)-N'-(4-isomenthyloxyphenyl)urea,
(65) N-benzoyl-N'-(4-neomenthyloxyphenyl)urea,
(66) N-(2-chlorobenzoyl)-N-(4-neomenthyloxyphenyl)urea,
(67) N-(2,6-difluorobenzoyl)-N'-(4-neomenthyloxyphenyl)urea,
(68) N-(2-chlorobenzoyl)-N'-(4-dl-isopinocamphenoxyphenyl)urea, and
(69) N-(2,6-difluorobenzoyl)-N'-(4-dl-isopinocamphenoxyphenyl)urea.

The substances according to the invention may be used for the control of mites and insects in agriculture and horticulture, in forests and in surface waters, as well as for the protection of textile agains attack by, for example, moths and carpet beetles, agains insects in stocks, for example, in stored cereals, and aginst insects in the veterinary and medical-hygienic sectors.

The substances according to the invention may also be used for the control of insects living in the manure of warm-blooded animals, such as cows, pigs and hens. for this application the active compounds can be administered orally to the animals, for example, mixed through the food, so that they end up in the manure after some time ("through-feeding").

The compounds according to the invention are particularly active against larvae and eggs of insects. In principle, the compounds may be used against all insects mentioned in Pestic. Sci. 9, 373-386 (1978).

For practical pesticidal application the substances in accordance with the invention are usually processed to compositions. In such compositions the active substance is mixed with solid carrier material or dissolved or dispersed in liquid carrier material, if desired in combination with auxiliary substances, for example, emulsifiers, wetting agents, dispersible agents and stabilizers.

Examples of compositions according to the invention are aqueous solutions and dispersions, oily solutions and oily dispersions, solutions in organic solvents, pastes, dusting powders, dispersible powders, miscible oils, granules, pellets and aerosol compositions.

Dispersible powders, pastes and miscible oils are compositions in concentrate form which are diluted prior to or during use.

The invert emulsions and solutions in organic solvents are mainly used in air application, namely when large areas are treated with a comparatively small quantity of composition. The invert emulsion can be prepared shortly before or even during spraying in the spraying appratus by emulsifying water in an oily solution or an oily dispersion of the active substance. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marlow), organic granules (for example, dried coffee grounds, cut tobaccostems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers, and glomulating the mixture then to the desired particle size.

Dusting powders can be obtained by intimately mixing the active substance with an inert solid powdered carrier material, for example talcum.

Dispersible powders are prepared by mixing 10 to 80 parts by weight of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignin sulphonates of alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally, if desired, other additives.

For the preparation of miscible oils the active compound is dissolved in a suitable solvent which preferably is poorly water-miscible, and one or more emulsifiers are added to this solution. Suitable solvents are, for example, xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, a glycol ether, dimethylformamide, or N-methylpyrrolidone, to which solution a dispersing agent, and if desired, a surface-active substance has been added. When diluting with water shortly before or during spraying, an aqueous dispersion of the active substances is then obtained.

An aerosol composition according to the invention is obtained in the usual manner by incorporation the active substance, if desired in a solvent, in a volatile liquid to be used as a propellant, for example, a mixture of chlorine-fluorine derivatives of methane and ethane, a mixture of lower hydrocarbons, dimethyl ether, or gases such as carbon dioxide, nitrogen and nitrous oxide.

Fumigating candles or fumigating powders, i.e. compositions which, while burning, can generate a pesticidal smoke, are obtained by taking up the active substance in a combustible mixture which may contain as a fuel a sugar or a wood, preferably in a ground form, a substance to maintain combustion, for example, ammonium nitrate or potassium chlorate, and furthermore a substance to delay combustion, for example, kaolin, bentonite and/or colloidal silicic acid.

In addition to the above-mentioned ingredients, the agents according to the invention may also contain other substances known for use in this type of agents. For example a lubricant, e.g., calcium stearate or magnesium stearate, may be added to a dispersible powder or a mixture to be granulated. "Adhesives", for example, polyvinylalcohol, cellulose derivatives or other colloidal materials, such as casein, may also be added so as to improve the adhesion of the pesticide to the crop. Furthermore, a substance may be added to reduce the phytotoxicity of the active substance, carrier material or auxiliary substance, for example, wool fat or wool fatty alcohol.

Other pesticidal compounds known per se may also be incorporated in the compositions according to the invention. As a result of this the activity spectrum of the composition is widened and synergism may occur.

For use in such a combination composition are to be considered, in addition to insecticidal and acaricidal compounds known per se, the following known growth regulating and fungicidal compounds:

Insectides, for example 1. organic chlorine compounds, for example 6,7,8,9,10,10-hexachloro-1,5,5a,6,9a-hexahydro-6,9-methanol-2,4,3-benzo[e]-dioxathiepine-3-oxide;
2. carbamates, for example, 2-dimethylamino-5,6-dimethylpyrimidin-4-yl dimethyl carbamate and 2-isopropoxyphenyl methylcarbamate;
3. di(m)ethylphosphates, for example, 2-chloro-2-diethylcarbamoyl-1-methylvinyl-, 2-methoxycarbonyl-1-methylvinyl-, 2-chloro-1-(2,4-dichlorophenyl)vinyl-, and 2-chloro-1-(2,4,5-trichlorophenyl)vinyl di(m)ethylphosphate;

4. O,O-di(m)methyl phosphorothioates, for example, O(S)-2-methylthioethyl-, S-2-ethylsulphinylethyl-, S-2-(1-methylcarbamoylethylthio)ethyl-, O-4-bromo-2,5-dichlorophenyl-, O-3,5,6-trichloro-2-pyridyl-, O-2-isopropyl-6-methylpyrimidin-4-yl-, and O-4-nitrophenyl O,O-di(m)ethyl phosphorothioate;

5. O,O-di(m)ethyl phosphorodithioates, for example, S-methylcarbamoylmethyl-, S-2-ethylthioethyl-, S-(3,4-dihydro-4-oxobenzo[d]-1,2,3-triazin-3-ylmethyl)-, S-1,2-di(ethoxycarbonyl)ethyl-, S-6-chloro-2-oxobenzoxazolin-3-ylmethyl-, and S-2,3-dihydro-5-methoxy-2-oxo-1,3,4-thiadiazol-3-ylmethyl O,O-di(m)ethylphosphorodithioate;

6. phosphonates, for example, dimethyl 2,2,2-trichloro-1-hydroxyethylphosphonate;

7. natural and synthetic pyrethroids;

8. amidines, for example, N'-(2-methyl-4-chlorophenyl)-N,N-dimethylformamidine;

9. microbial insecticides, such as *Bacilus thuringiensis*;

10. carbamoyl-oximes, such as S-methyl N-(methylcarbamoyloxy)thioacetamidate; and 11. other benzoylurea compounds, such as N-(2,6-difluorobenzoyl)-N'-(4-chlorophenyl)urea.

Acaricides, for example 1. organic tin compounds, for example, tricyclohexyl tin hydroxide and di[tri-(2-methyl-2-phenylpropyl)tin-]oxide;

2. organic halogen compounds, for example isopropyl 4,4'-dibromobenzilate, 2,2,2-trichloro-1,1-di(4-chlorphenyl)ethanol and 2,4,5,4'-tetrachlorodiphenyl sulphone;

3. synthetic pyrethroids, and furthermore: 3-chloro-α-ethoxyimino-2,6-dimethoxybenzyl benzoate and O,O-dimethyl S-methylcarbamoyl methyl phosphorothioate.

Fungicides, for example 1. organic tin compounds, for example, triphenyl tin hydroxide and triphenyl tin acetate;

2. alkylene bisdithiocarbamates, for example, zinc ethylenebisdithiocarbamate and manganese ethylene bisdithiocarbamate;

3. 1-acyl- or 1-carbamoyl-N-benzimidazole (-2) carbamates and 1,2-bis(3-alkoxycarbonyl-2-thiureido)benzene; and furthermore 2,4-dinitro-6-(2-octylphenyl-crotonate); 1-[bis(dimethylamino)phosphoryl]-3-phenyl-5-amino-1,2,4-triazole; N-trichloromethylthiophthalimide; N-trichloromethylthiotetrahydrophthalimide; N-(1,1,2,2-tetrachloroethylthio)-tetrahydrophthalimide; N-dichlorofluoromethylthio-N-phenyl-N,N'-dimethylsulphamide; tetrachloroisophthalonitrile; 2-(4'-thiazolyl)-benzimidazole; 5-butyl-2-ethylamino-6-methylpyrimidine-4-yl-dimethylsulphamate; 1-(4-chlorophenoxy)-3,3-dimethyl-1(1,2,4-triazole-1-yl)-2-butanone; α-(2-chlorophenyl)-α-(4-chlorophenyl)-5-pyrimidinemethanol; 1-(isopropylcarbamoyl)-3-(3,5-dichlorophenyl)hydantoin; N-(1,1,2,2-tetrachloroethylthio)-4-cyclohexene-1,2-carboximide; N-trichloromethylmercapto-4-cyclohexene-1,2-dicarboximide; N-tridecyl-2,6-dimethylmorpholine; metal salts of ethylphosphite; and N-(2,6-dimethylphenyl-N-methoxyacetyl)alanine methylester; or mixtures of these compounds.

The dosages of the pesticidal composition according to the invention desired for practical application will, of course, depend on various factors, for example, application area, selected active material, composition form, nature and extent of the infection, and the weather conditions.

In general favourable results are achieved with a dosage which corresponds to 1 to 5,000 g of the active substance per hectare.

For the above-described "through-feeding" the active substance is mixed through the food in a quantity which is effective for insecticidal applications.

The compounds according to the invention are novel substances which can be prepared in a manner known per se for related compounds.

For example, the compounds according to the invention can be prepared by reacting a substituted aniline of the general formula

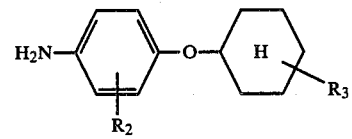

wherein $R_2$ and $R_3$ have the above meanings, with an isocyanate of the general formula

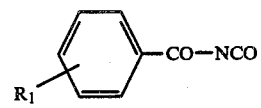

wherein $R_1$ also has the above meaning.

The novel compounds according to the invention can also be prepared by reacting a substituted benzamide of the general formula

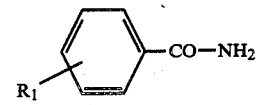

wherein $R_1$ has the above meaning, with an isocyanate of the general formula

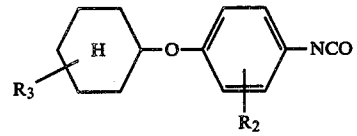

wherein $R_2$ and $R_3$ also have the above manings.

The above reactions are preferably carried out in the presence of an organic solvent, for example, an aromatic hydrocarbon, an alkyl halide, a cyclic or non-cyclic dialkyl ether, or acetonitrile, at a reaction temperature between 0° C. and the boiling-point of the solvent used.

Although the above-indicated methods of preparation are the best suitable, the novel compounds may be prepared in a still different way, for example, as described in the above-mentioned Netherlands Patent Application 7105350 or according to the methods described in Netherlands Patent Aplications 7806678 or 8005588.

EXAMPLE I

Preparation of
N-(2,6-difluorobenzoyl)-N'-(4-dl-menthyloxyphenyl-
)urea (1)

1.9 g of 2,6-difluorobenzoylisocyanate were added to a solution of 2.47 g of 4-dl-menthyloxy-aniline in a mixture of 15 ml of diethyl ether and 15 ml of petroleum ether (60–80) while stirring at room temperature. After adding 35 ml of petroleum ether (60–80), stirring was continued for another hour, after which the formed prepcipitate was sucked off, washed with petroleum ether and dried. The desired product was obtained in a yield of 4.1 g; melting-point 189°–190° C. The starting aniline was obtained from the corresponding nitro compound by reduction with hydrogen under the influence of Raney nickel as a catalyst, ethyl acetate being used as a solvent. 1-Nitro-4-dl-menthyloxybenzene was prepared by reaction of dl-menthol with 1-fluoro-4-nitrobenzene in tert.-butanol as a solvent in the presence of potassium tert.-butoxide.

In a corresponding manner, in which, if desired, instead of diethyl ether acetonitrile was used as a solvent for the urea-formation, the following compounds were prepared; the compound numbers correspond with the numbers given before in the specification:

| compound no. | melting point | compound no. | melting point |
| --- | --- | --- | --- |
| 2 | 192–194° C. | 31 | 181–189° C. |
| 3 | 129–132° C. | 32 | 179–182° C. |
| 4 | 152–154° C. | 33 | 216–217° C. |
| 5 | 186–188° C. | 34 | 189–190° C. |
| 6 | 155–157° C. | 35 | 186–190° C. |
| 7 | 154–156° C. | 36 | 183–185° C. |
| 8 | 199–201° C. | 37 | 158–160° C. |
| 9 | 176–182° C. | 38 | 139–143° C. |
| 10 | 183–186° C. | 39 | 181–185° C. |
| 11 | 165–171° C. | 40 | 182–187° C. |
| 12 | 189–193° C. | 41 | 164–170° C. |
| 13 | 175–177° C. | 42 | 188–192° C. |
| 14 | 201–204° C. | 43 | 190–192° C. |
| 15 | 189–193° C. | 44 | 185–188° C. |
| 16 | 166–169° C. | 45 | 218–220° C. |
| 17 | 184–189° C. | 46 | 205–207° C. |
| 18 | 176–180° C. | 47 | 214–214.5° C. |
| 19 | 153–156° C. | 48 | 214–215.4° C. |
| 20 | 171–172.5° C. | 49 | 220–222° C. |
| 21 | 132–136° C. | 58 | 196–202° C. |
| 22 | 142–146° C. | 59 | 182–183° C. |
| 23 | 160–163° C. | 60 | 201–205° C. |
| 24 | 184–188° C. | 61 | 179–183° C. |
| 25 | 187–189° C. | 62 | 174–175° C. |
| 26 | 205–208° C. | 63 | 146–147° C. |
| 27 | 158–166° C. | 64 | 146–147° C. |
| 28 | 148–160° C. | 65 | 206–207° C. |
| 29 | 155–175° C. | 66 | 194–195° C. |
| 30 | 148–163° C. | 67 | 215–216° C. |
|  |  | 68 | 192–193° C. |
|  |  | 69 | 184–185° C. |

EXAMPLE II

Preparation of
N-(4-fluorobenzoyl)-N'-(4-dl-menthyloxyphenyl)urea
(53)

2.75 g of 4-dl-menthyloxyphenylisocyanate were added to a solution of 1.4 g of 4-fluorobenzamide in 30 ml of xylene. The mixture was refluxed during 4 hours. After cooling down the formed precipitate was sucked off, washed with diethylether, and dried. The desired product was obtained in a yield of 2.9 g; melting point 203°–204° C. The starting isocyanate was obtained from 4-dl-menthyloxy-aniline (prepared as described in EXAMPLE I) by a reaction with phosgene in boiling toluene; purification by distillation.

In a corresponding manner the following compounds were prepared; the compound numbers correspond again with the numbers given before in the specification:

| compound no. | melting point | compound no. | melting point |
| --- | --- | --- | --- |
| 50 | 223–224° C. | 55 | 218–222° C. |
| 51 | 221–222° C. | 56 | 187–188° C. |
| 52 | 138–145° C. | 57 | 166–167° C. |
| 54 | 196–199° C. |  |  |

EXAMPLE III (a) Preparation of a solution of an active substance, namely
N-(2,6-difluorobenzoyl)-N'-(4-dl-menthyloxyphenyl-
)urea, in a water-miscible liquid ("liquid")

10 g of the above active substance were dissolved in a mixture of 10 ml of isophorone and approximately 70 ml of dimethylformamide, after which polyoxyethylene glycol ricinyl ether as an emulsifier was added in a quantity of 10 g.

The other active substances were processed to 10% or 20% "liquids" in a corresponding manner. In a corresponding manner, "liquids" were obtained in N-methylpyrrolidone, dimethylformamide, and a mixture of N-methylpyrrolidone and isophorone as solvents.

(b) Preparation of a solution of the active substance in an organic solvent 200 mg of the active substance to be investigated were dissolved in 1,000 ml of acetone in the presence of 1.6 g of nonylphenolpolyoxyethylene. After pouring in water, this solution may be used as a spraying liquid.

(c) Preparation of an emulsifiable concentrate of the active substance 10 g of the active substance to be investigated were dissolved in a mixture of 15 ml of isophorone and 70 ml of xylene; 5 g of a mixture of a polyoxyethylene sorbitan ester and an alkyl benzene sulphonate as an emulsifier were added to this solution.

(d) Preparation of a dispersible powder (W.P.) of the active substance 25 g of the active substance to be investigated were mixed with 68 g of kaolin in the presence of 2 g of sodium butylnaphthalene sulphonate and 5 g of lignin sulphonate.

(e) Preparation of a suspension concentrate (flowable) of the active substance

A mixture of 10 g of active substance, 2 g of lignin sulphonate and 0.8 g of sodium alkylsulphate were supplied with water till a total amount of 100 ml.

(f) Preparation of a granule of the active substance 7.5 g of active substance, 5 g of sulphite lye and 87.5 g of ground dolomite were mixed, after which the resulting mixture ws processed to a granular composition by means of the so-called compacting method.

EXAMPLE IV

Young Brussels sprouts plants, approximately 15 cm high, were sprayed with compositions obtained according to EXAMPLE III (b) in various concetrations; to these compositions had been added in addition approximately 250 mg of an alkylated phenol polyoxyethylene compound (Citowett) per liter. After the plants had dried, they were placed in cylinders of plexiglass and then infected with 5 larvae of *Pieris brassicae* (caterpillars of the cabbage white butterfly) in the third larval stage (L3). The cylinders were then covered with a gause and stored, an alternating light-dark cycle of 16 hours and 8 hours dark being used; temperature in the ligth 24° C., rel. humidity (RH) 70%; temperature in the dark 19° C., 80–90 RH. After 5 days the mortality percentage of the larvae was established. Each experiment was carried out in triplicate. The average results of the experiments are recorded in Table A below. The meanings of the symbols in the table are as follows:

+ = 90–100% mortality
± = 50–90% mortality
− = <50% mortality

N-(2-chlorobenzoyl)-N'-4-(1-phenylcyclohexyloxy)-phenyl urea ("known") has been included in the test by way of comparison.

TABLE A

| Compd. no | \multicolumn{9}{c}{Insecticidal activity against larvae (L3) of *Pieris brassicae* Concentration in mg of active substance per liter} |
|---|---|---|---|---|---|---|---|---|---|
| | 300 | 100 | 30 | 10 | 3 | 1 | 0.3 | 0.1 | 0.03 |
| (1) | + | + | + | + | + | + | + | + | − |
| (2) | + | + | + | + | + | + | + | + | − |
| (3) | + | + | + | + | + | + | + | + | − |
| (4) | + | + | + | + | + | + | + | + | − |
| (5) | + | + | + | + | + | + | + | + | − |
| (6) | + | + | + | + | + | + | + | + | − |
| (7) | + | + | + | + | + | + | + | + | − |
| (8) | + | + | + | + | + | + | ± | − | |
| (9) | + | + | + | + | + | + | − | | |
| (10) | + | + | + | + | + | + | + | − | |
| (11) | + | + | + | + | + | + | + | − | |
| (12) | + | + | + | + | + | + | − | | |
| (13) | + | + | + | + | + | + | + | − | |
| (14) | + | + | + | + | + | + | + | ± | − |
| (15) | + | + | + | + | ± | − | | | |
| (16) | + | + | + | + | ± | − | | | |
| (17) | + | + | + | + | + | + | + | + | − |
| (18) | + | + | + | + | + | + | ± | − | |
| (19) | + | + | + | + | + | ± | − | | |
| (20) | + | + | + | + | + | + | + | ± | − |
| (21) | + | + | + | + | + | − | | | |
| (22) | + | + | + | + | + | + | + | ± | − |
| (23) | + | + | + | + | + | + | + | + | ± |
| (24) | + | + | + | + | − | | | | |
| (25) | + | + | + | + | + | + | − | | |
| (26) | + | + | + | + | + | + | + | − | |
| (28) | + | + | + | + | + | + | − | | |
| (29) | + | + | + | + | + | + | + | − | |
| (30) | + | + | + | + | + | + | + | − | |
| (31) | + | + | + | + | + | + | + | + | − |
| (32) | + | + | + | + | + | + | ± | − | |
| (33) | + | + | + | + | + | + | + | − | |
| (34) | + | + | + | + | − | | | | |
| (35) | + | + | + | + | + | + | + | + | − |
| (36) | + | + | + | + | + | + | + | + | − |
| (39) | + | + | + | + | + | − | | | |
| (40) | + | + | + | + | + | + | − | | |
| (41) | + | + | + | + | + | + | − | | |
| (42) | + | + | + | + | + | + | + | − | |
| (44) | + | + | + | + | − | | | | |
| (45) | + | + | + | + | + | + | + | − | |
| (46) | + | + | + | + | + | + | + | − | |
| (48) | + | + | + | + | + | + | − | | |
| (49) | + | + | + | + | + | + | + | ± | − |
| (53) | + | + | + | + | + | + | − | | |
| (57) | + | + | + | + | + | + | + | ± | − |
| (58) | + | + | + | + | + | | | | |
| (59) | + | + | + | + | + | ± | − | | |
| (60) | + | + | + | + | + | + | − | | |
| (61) | + | + | + | + | + | + | − | | |
| (62) | + | + | + | + | + | ± | − | | |
| (63) | + | + | + | + | + | | | | |
| (64) | + | + | + | + | + | + | + | + | − |
| (65) | + | + | + | + | ± | − | | | |
| (66) | + | + | + | + | + | | | | |
| (67) | + | + | + | + | + | + | + | − | |
| (68) | + | + | + | + | + | + | ± | − | |
| (69) | + | + | + | + | + | + | + | | |
| "known" | + | + | − | | | | | | |

Note:
If the test results do not finish with a "−" sign, the tests have not been completed.

Liquid insecticidal compositions are used in practice in quantities of approximately 1,000 liters per hectare. The coverage of the plants with the composition, however, is considerably less good in practice than in a laboratory or glasshouse experiment as described herein before. It has hence been found that in practice the dose is to be increased by a factor 10 to obtain the same efficiency.

So in practical applications the above quantities with insecticidal activity correspond to approximately 1 to approximately 3,000 g of active substance per hectare.

EXAMPLE V

20 Larvae of *Aedes aegypti* (larvae of the yellow-fever mosquito) were placed in various concentrations of aqueous suspensions of the active substances obtained according to EXAMPLE III(e). The suspensions were kept at a temperature of 25° C. for 10 days, during which incubation period the larvae were fed with an aqueous suspension of powdered brown bread and yeast. After 10 days the mortality percentage was determined taking the natural mortality into account. The results of the experiment are recorded in Table B. The meanings of the symbols is the same as in EXAMPLE IV.

TABLE B

| Compd. no. | \multicolumn{7}{c}{Insecticidal activity against larvae (L1) of *Aedes aegypti* Concentration in mg of active substance per liter} |
|---|---|---|---|---|---|---|---|
| | 1 | 0.3 | 0.1 | 0.03 | 0.01 | 0.003 | 0.001 |
| (1) | + | + | + | + | + | ± | − |
| (2) | + | + | + | + | + | + | ± |
| (3) | + | + | + | + | + | − | |
| (4) | + | + | + | + | + | + | − |
| (5) | + | + | + | + | + | + | ± |
| (6) | + | + | + | + | + | − | |
| (7) | + | + | + | + | ± | − | |
| (10) | + | + | + | | | | |
| (11) | + | + | + | + | + | + | ± |
| (13) | + | + | + | | | | |
| (14) | + | + | + | | | | |
| (17) | + | + | + | + | − | | |
| (18) | + | + | + | − | | | |
| (19) | + | + | − | | | | |
| (20) | + | + | + | + | ± | ± | − |
| (22) | + | + | + | + | ± | − | |
| (23) | + | + | + | + | + | + | − |
| (25) | + | + | ± | − | | | |
| (26) | + | + | + | + | + | − | |
| (28) | + | + | ± | − | | | |
| (29) | + | + | + | + | − | | |
| (30) | + | + | + | + | ± | − | |
| (31) | + | + | + | + | + | ± | − |
| (33) | + | + | − | | | | |

TABLE B-continued

Insecticidal activity against larvae (L1) of *Aedes aegypti*

| Compd. no. | Concentration in mg of active substance per liter | | | | | | |
|---|---|---|---|---|---|---|---|
| | 1 | 0.3 | 0.1 | 0.03 | 0.01 | 0.003 | 0.001 |
| (38) | + | + | + | + | − | | |
| (39) | + | + | + | + | + | ± | − |
| (41) | + | + | + | + | − | | |
| (42) | + | + | + | + | + | ± | − |
| (48) | + | + | ± | − | | | |
| (49) | + | + | ± | − | | | |
| (58) | + | + | + | ± | − | | |
| (59) | + | + | + | + | + | − | |
| (61) | + | + | + | + | + | + | − |
| (63) | + | + | + | + | − | | |
| (64) | + | + | + | + | + | ± | − |
| (69) | + | + | + | + | + | + | − |

EXAMPLE VI

The growth tops of broad beans having four well developed leaves were removed, after which the plants were sprayed until dripping with compositions obtained according to EXAMPLE III(b) in various concentrations; to these compositions has moreover been added approximately 250 mg of Citowett per liter. After the plants had dried, they were placed in perspex cylinders and then infected with 5 larvae of *Spodoptera littoralis* (Egyptian cotton caterpillar) in the third laraval stage (L3). The cylinders were then covered with a gauze and then stored as described in EXAMPLE IV. After 5 days the mortality percentage of the larvae was established. Each experiment was carried out in triplicate. The average results of the experiments are recorded in table C. The meanings of the symbols are the same as in EXAMPLE IV.

TABLE C

Insecticidal activity against larvae (L3) of *Spodoptera littoralis*

| Compd. no. | Concentration in mg of active substance per liter | | | | | | | |
|---|---|---|---|---|---|---|---|---|
| | 300 | 100 | 30 | 10 | 3 | 1 | 0.3 | 0.1 |
| (1) | + | + | + | + | + | + | + | ± |
| (2) | + | + | + | + | + | ± | − | |
| (3) | + | + | + | + | + | + | + | ± |
| (4) | + | + | + | + | + | + | − | |
| (5) | + | + | + | + | + | + | − | |
| (7) | + | + | + | + | + | + | − | |
| (8) | + | + | + | + | + | + | − | |
| (9) | + | + | + | + | ± | − | | |
| (10) | + | + | + | + | + | ± | − | |
| (11) | + | + | + | + | + | + | − | |
| (12) | + | + | + | + | + | ± | − | |
| (13) | + | + | + | + | + | + | − | |
| (14) | + | + | + | + | + | + | − | |
| (22) | + | + | + | ± | − | | | |
| (23) | + | + | ± | ± | − | | | |
| (38) | + | + | + | + | ± | − | | |
| (39) | + | + | + | + | + | − | | |
| (40) | + | + | + | ± | − | | | |
| (41) | + | + | + | + | + | + | − | |
| (42) | + | + | + | + | + | ± | − | |
| (45) | + | + | + | ± | − | | | |
| (46) | + | + | + | + | + | − | | |
| (50) | + | + | + | + | + | − | | |
| (53) | + | + | + | + | + | + | − | |
| (56) | + | + | + | ± | − | | | |
| (57) | + | + | + | + | + | + | ± | − |
| (58) | + | + | + | + | + | − | | |
| (59) | + | + | + | + | + | ± | − | |
| (60) | + | + | + | + | − | | | |
| (61) | + | + | + | + | − | | | |
| (62) | + | + | + | + | ± | − | | |
| (63) | + | + | + | + | + | ± | | |
| (64) | + | + | + | + | ± | ± | − | |
| (65) | + | + | + | ± | ± | − | | |
| (66) | + | + | + | + | + | − | | |

TABLE C-continued

Insecticidal activity against larvae (L3) of *Spodoptera littoralis*

| Compd. no. | Concentration in mg of active substance per liter | | | | | | | |
|---|---|---|---|---|---|---|---|---|
| | 300 | 100 | 30 | 10 | 3 | 1 | 0.3 | 0.1 |
| (67) | + | + | + | + | ± | − | | |
| (68) | + | + | + | ± | − | | | |
| (69) | + | + | + | + | + | − | | |

In practice the above quantities with insecticidal activity correspond to approx. 3 to approx 3,000 g of active substance per hectare.

EXAMPLE VII

Young potato plants, approx 15 cm high, were sprayed with the compositions obtained according to EXAMPLE III(b) in various concentrations; in addition approx. 250 mg of Citowett per liter had been added to these compositions. After the plants had dried, plexiglass cylinders were placed over the plants. The plants were then infected with 10 larvae of *Leptinotarsa decemlineata* (larvae of the Colorado beetle) in the third larval stage (L3). The infected plants were stored as indicated in EXAMPLE IV. After 5 days the mortality percentage of the larvae was established. The experiments have been carried out in triplicate. The average results of the experiments are recorded in table D below. The meanings of the symbols are the same as in EXAMPLE IV. The same "known" compound was used as in EXAMPLE IV.

TABLE D

Insecticidal activity against larvae of *Leptinotarsa decemlineata*

| Compd. no. | Concentration in mg of active substance per liter | | | | | | | |
|---|---|---|---|---|---|---|---|---|
| | 300 | 100 | 30 | 10 | 3 | 1 | 0.3 | 0.1 |
| (1) | ± | ± | ± | ± | ± | ± | ± | − |
| (2) | + | + | + | + | ± | − | | |
| (3) | ± | ± | ± | ± | ± | ± | − | |
| (4) | + | + | + | ± | − | | | |
| (5) | + | + | + | ± | − | | | |
| (6) | + | + | + | ± | − | | | |
| (7) | ± | ± | ± | ± | ± | − | | |
| (8) | + | + | + | − | | | | |
| (9) | + | + | ± | ± | − | | | |
| (10) | + | + | + | + | ± | ± | − | |
| (11) | + | + | + | + | + | ± | − | |
| (12) | + | + | + | ± | − | | | |
| (13) | + | + | + | + | + | + | − | |
| (14) | + | + | + | + | + | + | ± | − |
| (17) | ± | ± | ± | ± | − | | | |
| (18) | ± | ± | − | | | | | |
| (20) | ± | ± | ± | ± | ± | ± | − | |
| (22) | + | + | + | + | − | | | |
| (23) | + | + | + | + | + | − | | |
| (38) | + | + | + | − | | | | |
| (39) | + | + | + | − | | | | |
| (41) | + | + | + | − | | | | |
| (45) | + | + | + | ± | ± | − | | |
| (46) | + | + | + | + | + | ± | − | |
| (49) | + | + | + | ± | ± | − | | |
| (57) | ± | ± | ± | ± | − | | | |
| (58) | + | + | + | ± | − | | | |
| (59) | + | + | + | + | − | | | |
| (60) | + | + | + | + | − | | | |
| (61) | + | + | + | + | ± | − | | |
| (63) | + | + | + | + | − | | | |
| (64) | + | + | + | + | + | ± | − | |
| (66) | + | + | + | − | | | | |
| (67) | + | + | + | + | − | | | |
| (68) | + | + | + | ± | − | | | |
| (69) | + | + | + | + | ± | − | | |
| "known" | − | | | | | | | |

EXAMPLE VIII

Dwarf French bean plants (*Phaseolus vulgaris*) having two well developed leaves were infected with *Tetranychus Cinnabarinus* (carnation spider mite) by placing a given number of adult female mites on the plants. Two days after the infection the plants with the adult mites present thereon were sprayed till dripping with compositions obtained according to EXAMPLE III(b) in various concentrations; to these compositions had moreover been added approximately 150 mg of an alkylated phenolpolyoxyethylene compound (Citowett) per liter. 5 Days after spraying, the adult insects were removed from the plants. The plants were stored for 2 weeks in a space with controlled temperature (T) and air humidity (AH), an alternating light-dark cycle being used of 16 hours light and 8 hours dark. Ligt: T approximately 24° C., AH approximately 70%; dark: T approximately 19° C., AH 80–90%. The reduction of the population, i.e. the mortality of the number of larve and eggs as compared with plants not treated with chemicals was established. The experiment was carried out in triplicate.

When using a composition which contained N-(2,6-difluorobenzoyl)-N'-(4-dl-menthylphenyl)urea (1) as the active substance, a significant reduction of the population as compared with plants not treated with chemicals was found.

We claim:

1. Compounds of the formula

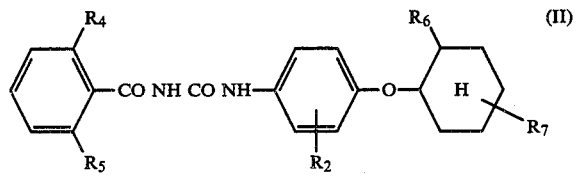

wherein

R$_2$ is a hydrogen atom or represents 1 or 2 substituents selected from the group consisting of chlorine, methyl and trifluoromethyl, R$_4$ is a halogen atom or a methyl group, R$_5$ is a hydrogen atom or a halogen atom, R$_6$ is an alkyl or alkenyl group having 1–4 or 2–4 carbon atoms respectively, and R$_7$ is a hydrogen atom or an alkyl or alkenyl group having 1–4 or 2–4 carbon atoms respectively, or wherein R$_6$ and R$_7$ together with the cyclohexyl ring to which they are attached form a 2-bornyl or a 2-adamantyl group.

2. Compounds of the formula

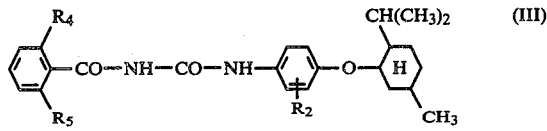

wherein

R$_2$ is a hydrogen atom or represents 1 or 2 substituents selected from the group consisting of chlorine, methyl and trifluoromethyl, and R$_4$ and R$_5$ have the meanings given in claim 1.

3. A compound selected from the group consisting of N-(2,6-difluorobenzoyl)-N'-(4-menthyloxyphenyl)urea, and N-(2-chlorobenzoyl-N'-(4-menthyloxyphenyl)urea.

4. A composition having insecticidal and acaricidal activity, characterized in that, in addition to a liquid or solid inert carrier material, the composition comprises a compound of the formula II as in claim 1, and wherein R$_2$, R$_4$, R$_5$, R$_6$ and R$_7$ have the meanings given in claim 1.

5. A composition having insecticidal and acaricidal activity, characterized in that, in addition to a liquid or solid inert carrier material the active constituent is a compound of the formula III as in claim 2, and wherein R$_2$, R$_4$ and R$_5$ have the meanings given in claim 2.

6. A composition as claimed in claim 4, characterized in that the active constituent is N-(2,6-difluorobenzoyl)-N'-(4-menthyloxyphenyl)urea or N-(2-chlorobenzoyl)-N'-(4-menthyloxyphenyl)urea.

7. A method of preparing a composition having insecticidal and acaricidal activity, characterized in that a compound of the formula II as in claim 1, and wherein R$_2$, R$_4$, R$_5$, R$_6$ and R$_7$ have the meanings given in claim 1, and is included into a liquid or solid inert carrier material, if desired while adding other pesticidal compounds, artificial manures and/or auxiliary substances such as wetting agents, emulsifiers, dispersible agents, and stabilizers.

8. A benzoylurea which is N-(2,6-difluorobenzoyl)-N'-(4-menthyloxyphenyl)urea.

9. A benzoylura which is N-(2-chlorobenzoyl)-N'-(4-menthyloxyphenyl)urea.

* * * * *